United States Patent [19]

North

[11] Patent Number: 5,776,966
[45] Date of Patent: Jul. 7, 1998

[54] SELECTIVE CELL INACTIVATION IN BLOOD

[75] Inventor: Janice North, Vancouver, Canada

[73] Assignees: University of British Columbia; Quadra Logic Technologies Inc., both of Vancouver, Canada

[21] Appl. No.: 889,707

[22] Filed: May 27, 1992

[51] Int. Cl.$^6$ ............................................ A61K 31/40
[52] U.S. Cl. ........................... 514/410; 514/885; 514/908
[58] Field of Search ............................................ 514/410

[56] References Cited

U.S. PATENT DOCUMENTS

| | | | |
|---|---|---|---|
| 4,610,241 | 9/1986 | Gordon | 128/1.3 |
| 4,960,408 | 10/1990 | Klainer et al. | 604/4 |
| 5,028,594 | 7/1991 | Carson | 514/23 |
| 5,087,636 | 2/1992 | Jamieson et al. | 514/410 |
| 5,095,030 | 3/1992 | Levy et al. | 514/410 |
| 5,149,708 | 9/1992 | Dolphin et al. | 514/410 |
| 5,171,749 | 12/1992 | Levy et al. | 514/410 |
| 5,190,966 | 3/1993 | Dougherty et al. | 514/410 |
| 5,214,036 | 5/1993 | Allison et al. | 514/185 |

OTHER PUBLICATIONS

Gruner et al., "Inhibition of HLA–DR Antigen Expression and of the Allogeneic Mixed Leukocyte Reaction by Photochemical Treatment", *Tissue Antigens* 27, 147 and 151–154 (1986).

North et al., "Photodynamic Inactivation of Retrovirus by Benzoporphyrin Derivative: a Feline Leukemia Virus Model", *Transfusion* 32, 121–28 (1992).

North et al., "Photoinactivation of Human Immunodeficiency Virus (HIV) by Benzoporphyrin Derivative", *Cell Biochem.*, Supp., Part E, 85, Abstract Q 545 (1992); and.

Matthews et al., "Preliminary Studies of Photoinactivation of Human Immunodeficiency Virus in Blood", *Transfusion* 31, 636–41 (1991).

Zarling et al., *J. Immunol.* (1990) 144:2992–2998.

Zuckerman et al., "Treatment of Antigen–induced Arthritis in Rabbits with Dysprosium–165–Ferric Hydroxide Macroaggregates", *J. of Orthopaedic Res.*, 7:50–60 (1989).

*Primary Examiner*—Richard L. Raymond
*Assistant Examiner*—Brian M. Burn
*Attorney, Agent, or Firm*—Morrison & Foerster

[57] ABSTRACT

Treatment with a set of porphyrin compounds using a photodynamic therapy approach is able selectively to lower elevated levels of activated leukocytes in a leukocyte population. This is particularly helpful in subjects containing such elevated levels of T-cell subsets, such as HIV-infected subjects.

12 Claims, 5 Drawing Sheets

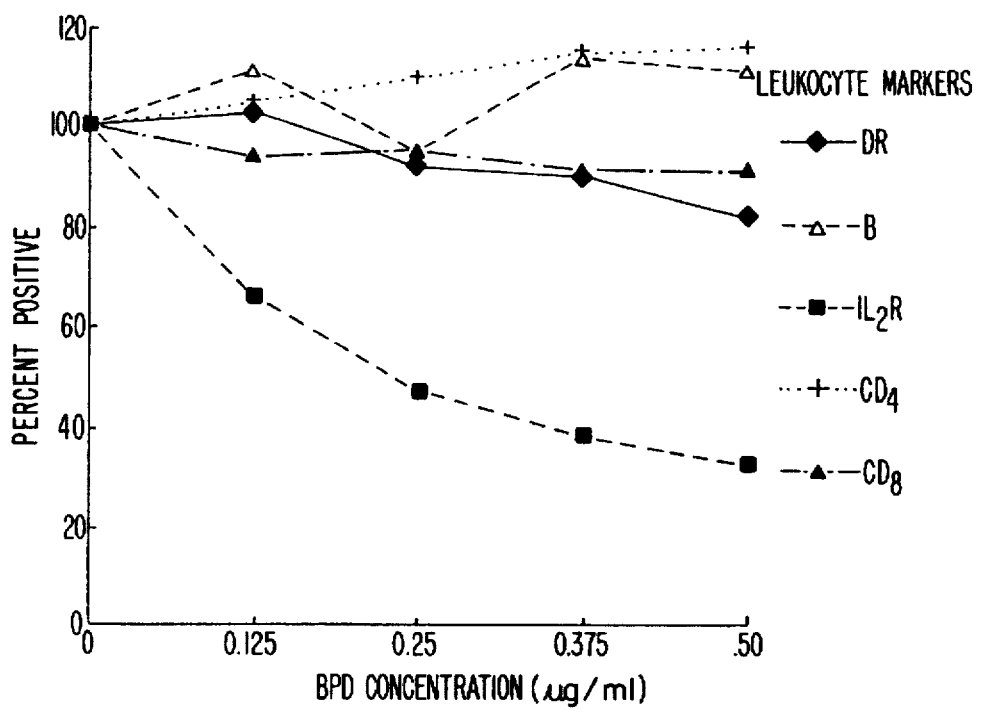
FIG. IA
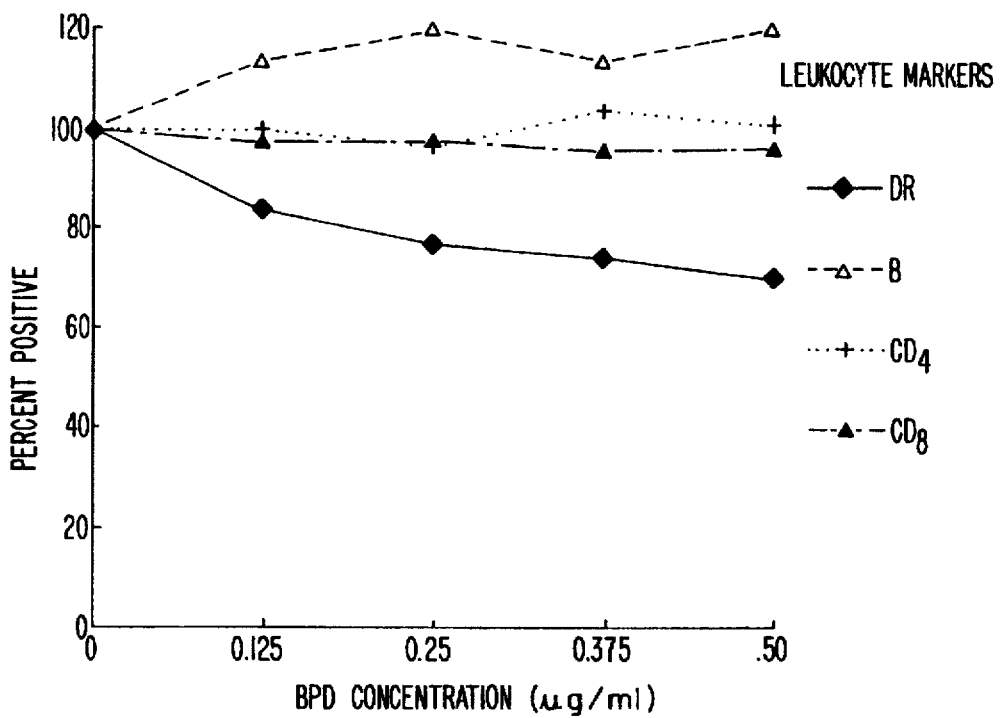
FIG. IB

BPD-DA

BPD-DB

BPD-MA

BPD-MB

SELECTIVE CELL INACTIVATION IN BLOOD

TECHNICAL FIELD

The invention relates to photodynamic methods for selectively depleting blood or bone marrow of cells important in the progress of certain diseases. More specifically, it concerns methods to reduce selectively the population of activated leukocytes in the blood or bone marrow of subjects with immune dysfunctional disorders, such as patients with autoimmune diseases or patients infected with HIV.

BACKGROUND ART

The immunodisturbances caused by the human immunodeficiency virus have been studied, but the nature of the progress of the disease is still uncertain. However, it has been shown that HIV-infected humans have circulating cytotoxic T-lymphocytes that lyse uninfected $CD4^+$ cells (Zarling, J. M. et al., *J Immunol* (1990) 144:2992. It is also generally understood that infection with HIV, while depleting the levels of $CD4^+$ cells, enhances the levels of $CD8^+$, $DR^+$, and $IL-2R^+$ leukocytes. $IL-2R^+$ is considered an activation marker and DR is an HLA marker, and these may be present on cells with additional markers such as CD4 and CD8.

One approach to interfering with the progress of this infection and resultant immunosuppression employs strategies to alter the composition of the blood with respect to various components of the immune system. In one attempt to achieve this, U.S. Pat. No. 4,960,408 discloses a process of treating a subject having AIDS-related complex systemically with psoralen, and then extracorporeally treating the T-lymphocytes with ultraviolet radiation of a wavelength absorbed by the psoralen compound. The irradiated T-cells are then returned. This treatment apparently enhances the levels of $CD3^+$ cells, $CD4^+$ cells, and $CD8^+$ cells, although not in a uniform fashion.

U.S. Pat. No. 5,095,030, issued 10 Mar. 1992, which is incorporated herein in its entirety by reference, discloses and claims various wavelength-specific cytotoxic agents which are generically described as "green porphyrins." These compounds are porphyrin derivatives which are modified by a Diels Alder reaction effectively to shift the wavelength of absorption to a longer wavelength. This results in some favorable properties as compared to, for example, hematoporphyrin derivative when these compounds are employed in photodynamic therapy generally. As described in this patent, these cytotoxic agents, when administered systemically, "home" to unwanted cells, in particular to tumor cells or pathogenic viruses and subsequent irradiation with light absorbed by these compounds causes them to transition in such a way as to effect cytotoxicity. It is not believed that the compounds themselves are chemically altered in this process.

It has now been found possible selectively to diminish the levels of activated leukocyte subsets which are associated with HIV infection or other immune dysfunction using the green porphyrin compounds described above. This depletion can be effected without side effects on the normally functioning B cell, $CD4^+$ cell, $CD8^+$ cell or NK cell populations. Either leukocytes after separation from red blood cells can be treated using the method of the invention or whole blood can be subjected to this treatment.

DISCLOSURE OF THE INVENTION

The invention provides a method selectively to lower the population of activated leukocytes in subjects showing elevated levels of leukocyte activation markers. The invention method involves treating a body fluid, i.e., bone marrow or blood or appropriate fraction thereof, with a specific class of agents useful in photodynamic therapy, followed by irradiating the blood or fraction with at least one wavelength absorbed by the therapeutic. The treatment can be conducted in vivo, entirely extracorporeally, or partially in vivo and partially ex vivo.

Thus, in one aspect, the invention is directed to a method selectively to reduce the activated leukocyte population in the body fluid of a subject in need of such reduction which method comprises:

treating said body fluid or an activated leukocyte-containing fraction thereof with an effective amount of a green porphyrin (Gp) compound; and irradiating said treated body fluid with light comprising at least one wavelength absorbed by said Gp compound.

In another aspect, the invention is directed to a method to treat an HIV-infected patient or other immune dysfunctional patient which method comprises treating at least a portion of said patient's body fluid or fraction thereof containing cells to be depleted with an effective amount of the Gp, followed by irradiation.

In still other aspects, the invention is directed to leukocyte-activated blood or plasma or other subfraction depleted of activated leukocytes, of HIV-infected cells, or of free HIV.

BRIEF DESCRIPTION OF THE DRAWINGS

FIGS. 1A and 1B show the effect of Gp and irradiation on various subsets of leukocytes having various markers including B-cells, $CD4^+$ cells, $CD8^+$ cells, $DR^+$ cells and $IL-2R^+$ cells in blood from two HIV-infected patients.

MODES OF CARRYING OUT THE INVENTION

Figure 2:
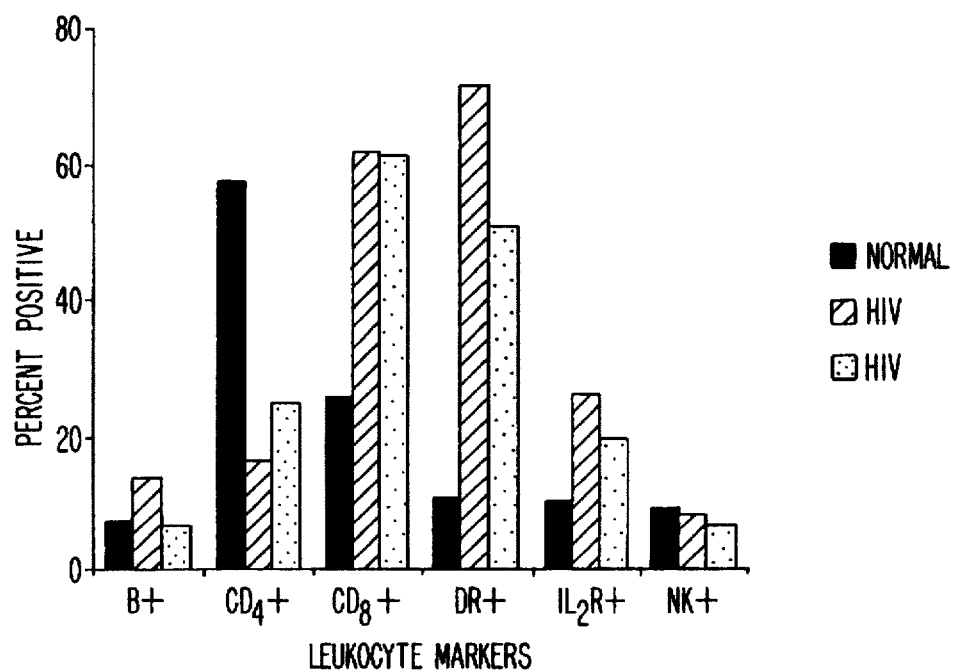
FIG. 2 shows the relative concentrations of the subsets of leukocytes in blood from a normal donor and from two HIV-infected patients.

The methods of the invention comprise the treatment of a body fluid, such as bone marrow or blood or appropriate fractions thereof containing abnormally elevated levels of endogenous, or infected endogenous, cells with a green porphyrin compound, followed by irradiation of the body fluid or fraction with radiation absorbed by the green porphyrin. The method of the invention can be conducted in a variety of protocols—the two essential elements are assuring that the green porphyrins are associated with the cells whose populations are to be diminished and that the green porphyrin associated with these cells is irradiated with the appropriate wavelength. As used herein, "body fluid" refers to body fluids which contain elevated levels of activated leukocytes or other cells, such as HIV-infected cells, to be depleted. Such body fluids are typically bone marrow or blood or fractions thereof.

While bone marrow can be used as the substrate for the method of the invention, the use of the patient's blood is often more convenient. Thus, in one protocol, whole blood is withdrawn from the subject and treated with a suitable concentration of the green porphyrin for a time period sufficient to permit the green porphyrin to be associated with the desired target cells. The whole blood is then irradiated in the extracorporeal container or apparatus with the appropriate wavelength and the treated irradiated blood returned to the patient.

Alternatively, the patient is administered the green porphyrin or mixtures thereof in suitable formulations, typically by injection but also by other routes of administration such as oral administration or transmucosal administration. After the green porphyrin has been given sufficient time to enter the bloodstream, a suitable radiation source can be applied to the body of the patient; for example, a catheterized fiber optic may be inserted into suitable positions in the bloodstream, or external transcutaneous light exposure may be employed. The blood is then irradiated in vivo.

Alternatively, the blood withdrawn from the patient can be separated into fractions, typically into a red blood cell fraction and a leukocyte-enriched plasma fraction and the leukocyte plasma treated with green porphyrin and irradiated before returning the plasma (and the red blood cells if desired) into the patient. Of course, the separation into fractions can be conducted at any point during the extracorporeal treatment so that the Gp could be added to the whole blood and the blood subsequently separated into red blood cells and leukocyte-enriched fractions before irradiation of the leukocyte-enriched fraction.

Suitable subjects for the treatment of the invention include HIV infected patients who have been shown to have elevated levels of activated leukocytes, such as $DR^+$ and $IL-2R^+$ cells in their blood. These levels can be diminished selectively by the method of the invention. Other patients who are expected to show elevated levels of these cells include patients showing unwanted immunoactivation generally, such as those who are subject to graft-versus-host disease or organ transplant rejection as a result, for example, of organ or bone marrow transplantation, and those who show autoimmune conditions such as rheumatoid arthritis, lupus erythematosus, muscular dystrophy, or myasthenia gravis. For transplantation, fluids from the donor organ or fluids from the patient recipient may be treated.

Typically, the green porphyrins are administered in such a way as to result in a final concentration in the fluid or fluid fraction to be treated of about 0.05–5 µg/ml, preferably about 0.1–1 µg/ml and most preferably about 0.5 µg/ml. The treated fluid or fluid fraction is then irradiated with light from any suitable source such as a laser diode, a lightemitting diode, fiber-optic-conducted laser light, and the like. Typical wavelengths are in the range of about 600–790 nm, preferably 630–710 nm, most preferably 690–780 nanometers and typical intensities are on the order of 1–50 $J/cm^2$, preferably about 5–25 $J/cm^2$ and most preferably around 8–15 $J/cm^2$. A wavelength range of 685–695 nm for these intensities is preferred. Irradiation is continued for about 2–180 minutes, preferably about 15–120 minutes depending on the nature and concentration of the green porphyrin, the amount of fluid treated, the susceptibility of the patient's cells, the intensity and wavelength of the light, and the method of irradiation (in vivo or ex vivo). Suitable optimization of the concentration of Gp and irradiation parameters is well within ordinary skill.

In further detail with respect to the green porphyrins useful in the invention, the general structures of typical green porphyrins are shown in FIG. 5. Particularly preferred forms are shown in FIG. 6.

The Gp is selected from a group of porphyrin derivatives obtained using Diels-Alder reactions of acetylene derivatives with protoporphyrin under conditions which effect a reaction at only one of the two available conjugated, nonaromatic diene structures present in the protoporphyrin-IX ring system (rings A and B). The formulas shown in FIGS. 5A–5F represent typical green porphyrins of the invention. These compounds are shown in the figure with hydrogen occupying the internal ring nitrogens; however, it is understood that the metalated forms wherein a cation replaces one or both of these hydrogens can also be employed. It is also understood that these compounds can be labeled either by replacement of one or more of the atoms in the structure by its radioactive form, or by coupling to a radioisotope such as a radioactive metal or, for example, a radioisotope of iodine.

Figure 5A:
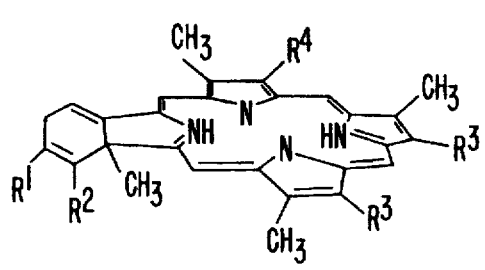
FIGS. 5A–5F show the generic structures of the various green porphyrins useful in the invention.
Figure 5B:
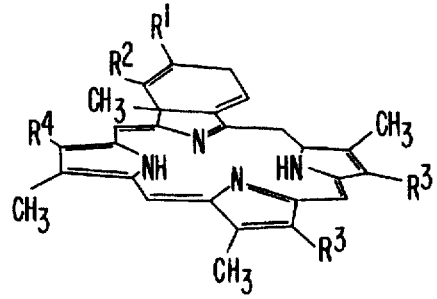
Figure 5C:
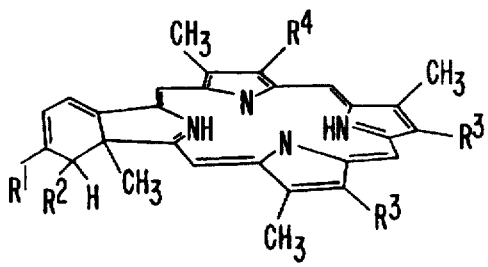
Figure 5D:
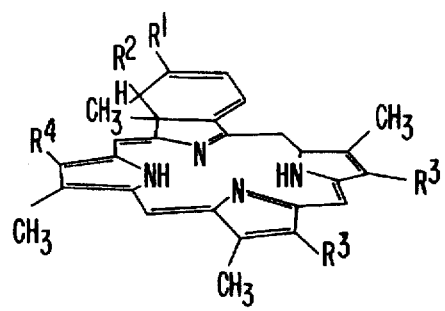

For convenience, an abbreviation of the term hydromonobenzoporphyrin derivative—"BPD"—is generally used to refer to compounds of FIGS. 5C and 5D, as these are the preferred forms of Gp.

Furthermore, dimeric forms of the Gp can be provided, thus amplifying the ability of the Gp compound to absorb light on a per mole basis. Dimeric and multimeric forms of Gp/porphyrin combinations can also be employed, providing additional absorption wavelengths.

The modified porphyrins (referred to as "green porphyrin" or "Gp" herein) can be conjugated to specific ligands reactive with a target, such as receptor-specific ligands or immunoglobulins or immunospecific portions of immunoglobulins, permitting them to be more concentrated in a desired target tissue or substances. This conjugation permits further lowering of the required dose levels since the material is not wasted in distribution into other tissues whose destruction, far from being desired, must be avoided.

When the Gp is irradiated in situ using light in the visible absorption range, photoactivation results in cytotoxicity to the surrounding tissue. While the absorption spectrum also includes shorter wavelengths, there is an especially useful absorption maximum in the 670–780 nm range.

In general, the position of wavelength absorption is achieved by effectively saturating one of the two π-bonds in one, but not two, of the four pyrrole rings which constitute the typical porphyrin system. In protoporphyrin-IX two of the pyrroles contain vinyl substitutions such that the exocyclic π-bond is conjugated to one of the two π-bonds in the ring. A Diels-Alder reaction involving one of these conjugated systems with an acetylene derivative dienophile results in a fused cyclohexadiene—referred to herein as "hydrobenzo"—fused to the A or B ring, as shown in FIGS. 5A and 5B. Rearrangement of the π system in the hexadiene ring results in the compounds of FIGS. 5C and 5D; reduction provides the compounds of FIGS. 5E and 5F. All of these compounds provide the desired bathochromic shift in absorption maximum.

Specific preparation of the Gp compounds useful in the invention is described in detail in the above-referenced U.S. Pat. No. 5,095,030.

For the compound shown in FIGS. 5 and 6, generally, $R^1$ and $R^2$ are each, independently, moderate electron-withdrawing substituents, and are, most commonly, carbalkoxy, or alkyl or aryl sulfonyl, or any other activating substituents, which are not sufficiently electron-withdrawing to result in reaction with both A and B rings rather than reaction with only one, such as cyano or —CONR$^5$CO— wherein R$^5$ is aryl or alkyl. One of R$^1$ and R$^2$ may optionally be H while the other is an electron withdrawing substituent of sufficient strength to facilitate the Diels-Alder reaction.

As used herein, carboxy is, as conventionally defined, —COOH and carbalkoxy is —COOR, wherein R is alkyl; carboxyalkyl refers to the substituent —R'—COOH wherein R' is alkylene; carbalkoxyalkyl refers to —R'—COOR wherein R' and R are alkylene and alkyl respectively. Alkyl is a saturated straight or branched chain hydrocarbyl of 1–6 carbon atoms such as methyl, n-hexyl, 2-methylpentyl, t-butyl, n-propyl, and so forth. Alkylene is as alkyl except that the group is divalent. Aryl or alkyl sulfonyl moieties have the formula SO$_2$R wherein R is alkyl as above-defined, or is aryl, wherein aryl is phenyl optionally substituted with 1–3 substituents independently selected from halo (fluoro, chloro, bromo or iodo), lower alkyl (1–4C) or lower alkoxy (1–4C). In addition, one or both R$^1$ of R$^2$ can itself be aryl—i.e., phenyl optionally substituted as above defined.

As shown in FIG. 5, the adduct formed by the reaction of R$^1$—C=C—R$^2$ with the protoporphyrin-IX ring system (R$^3$ is a protected form of 2-carboxyethyl such as 2-carbomethoxyethyl or 2-carboethoxyethyl; R$^4$ is CH=CH$_2$) are compounds of the FIGS. 5A and 5B wherein the compound in FIG. 5A results from addition to the A ring and FIG. 5B results from addition to the B ring. In these resulting products of FIGS. 5A and 5B, R$^4$ remains CH=CH$_2$, however this vinyl group is readily derivatized to other embodiments of R$^4$ by addition to or oxidation of the vinyl ring substituent of ring B in FIG. 5A or ring A in FIG. 5B. The addition or oxidation products can be further substituted if the added substituents are functional leaving groups—for example —Br may be substituted by —OH, —OR (R is alkyl 1–6C as above), or —NH$_2$, —NHR, —NR$_2$, etc. In preferred embodiments, one of the added substituents is hydrogen, and the other is selected from the group consisting of halo (fluoro, chloro, bromo or iodo), hydroxy, lower alkoxy, amino or an amide, sulfhydryl or an organo-sulfide or can be, itself, hydrogen. Addition to the vinyl group does not appreciably change the absorption spectrum of the resulting compound. The product of the Markonikov addition of water provides a substituent structure analogous to the hematoporphyrin ring system at the relevant ring. Thus, the compounds of the invention include various groups as R$^4$, including substituents which provide additional porphyrin or porphyrin-related ring systems, as will be further described below.

R$^3$ in protoporphyrin-IX is 2-carboxyethyl (—CH$_2$CH$_2$COOH). However, the nature of R$^3$ (unless it contains a π-bond conjugated to ring π-bond), is ordinarily not relevant to the progress of the Diels-Alder reaction or to the effectiveness and absorption spectrum of the resulting product. R$^3$ can thus be, for example, lower alkyl (1–4C), or 1-carboxyalkyl (2–6C) or the esters or amides thereof. The R$^3$ substituent may also be substituted with halogen as above-defined, or with other nonreactive substituents. However, as the convenient starting materials for the Gp compounds of the invention are the naturally occurring porphyrins, the preferred substituents for R$^3$ are CH$_2$CH$_2$COOH or —CH$_2$CHR$_2$COOR, wherein R is alkyl (1–6C).

In the BPD compounds of the invention, it has been found advantageous to hydrolyze or partially hydrolyze the esterified carboxy group in —CH$_2$CH$_2$COOR. The hydrolysis occurs at a much faster rate than that of the ester groups of R$^1$, R$^2$, and the solubility and biodistribution characteristics of the resulting compounds are more desirable than those of the unhydrolyzed form. Hydrolysis results in the diacid or monoacid products (or their salts).

The hydro-monobenzoporphyrins which directly result from the Diels-Alder reaction described in the cited references can also be isomerized to compounds of formulas shown as FIGS. 5C and 5D.

The depictions of compounds in FIGS. 5C and 5D do not show the relative position of the exocyclic methyl group (ring A of formula 3 and ring B of FIG. 5D) with respect to the R$^2$ substituent. Either isomer is available.

Figure 5E:
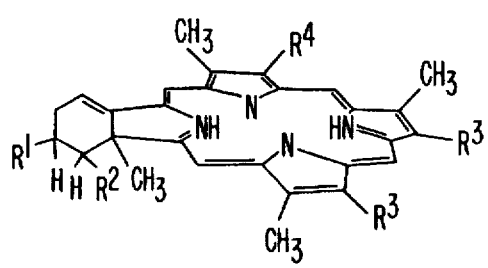
Figure 5F:
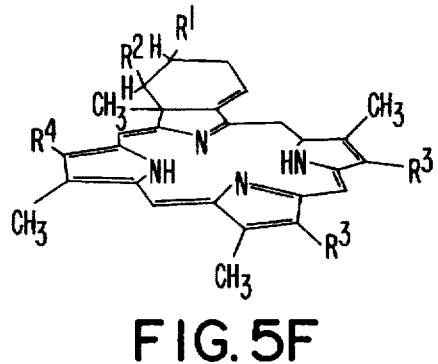

In addition, the Diels-Alder products can be selectively reduced by treating with hydrogen in the presence of palladium on charcoal to give the saturated ring analogs, shown as FIGS. 5E and 5F corresponding to the respective Diels-Alder products of rings A and B. These reduced products are less preferred embodiments, and are less useful in the method of the invention than the compounds of FIGS. 5A–5D.

The description set forth above with respect to the compounds of FIGS. 5A and 5B concerning derivatization by conversion of the remaining vinyl substituent (R$^4$) and with respect to variability of —R$^3$ applies as well to the compounds of FIGS. 5C, 5D, 5E and 5F.

The compounds of FIGS. 5C and 5D (BPD), and especially those which have hydrolyzed and partially hydrolyzed carbalkoxy groups in R$^3$, are most preferred. Compounds of the invention which contain —COOH may be prepared as the free acid or in the form of salts with organic or inorganic bases.

It will be noted that many of the compounds of FIGS. 5A–5F contain at least one chiral center and therefore exist as optical isomers. The conjugates and methods of the invention include compounds having both configurations of the chiral carbons, whether the compounds are supplied as isolates of a single stereoisomer or are mixtures of enantiomers and/or diastereomers. Separation of mixtures of diastereomers may be effected by any conventional means; mixtures of enantiomers may be separated by usual techniques of reacting them with optically active preparations and separating the resulting diastereomers.

It should further be noted that the reaction products may be unseparated mixtures of A and B ring additions, e.g., mixtures of FIGS. 5A and 5B or 5C and 5D or 5E and 6F. Either the separated forms—i.e., FIG. 5C alone or 5D alone, or mixtures in any ratio may be employed in the methods of therapy and diagnosis set forth herein.

FIGS. 6A–6D show four particularly preferred compounds of the invention which have not been previously described in the art. These compounds are collectively designated benzoporphyrin derivative (BPD) as they are forms of Gp having the formula of FIGS. 5C and 5D. These are hydrolyzed or partially hydrolyzed forms of the rearranged products of FIGS. 5C and 5D, wherein one or both of the protected carboxyl groups of R$^3$ are hydrolyzed. The ester groups at R$^1$ and R$^2$ hydrolyze relatively so slowly that conversion to the forms shown in FIG. 6 is easily effected.

For purposes of this description, R$^3$ is —CH$_2$CH$_2$COOR$^3$'. As shown in FIGS. 6A–6D, each R$^3$' is H in preferred compound BPD-DA. R$^1$ and R$^2$ are carbalkoxy, and derivatization is at ring A; BPD-DB is the corresponding compound wherein derivatization is at ring B. BPD-MA represents the partially hydrolyzed form of BPD- DA, and BPD-MB, the partially hydrolyzed form of BPD-DB. Thus, in these latter compounds, $R^1$ and $R^2$ are carbalkoxy, one $R^{3'}$ is H and the other $R^{3'}$ is alkyl (1–6C). The compounds of formulas BPD-MA and BPD-MB may be homogeneous wherein only the C ring carbalkoxyethyl or only the D ring carbalkoxyethyl is hydrolyzed, or may be mixtures of the C and D ring substituent hydrolyzates. In addition, mixtures of any two or more of BPD-MA, -MB, -DA and -DB may be employed in the method of the invention.

Certain other embodiments wherein $R^4$ is other than vinyl or wherein $R^3$ is a nonnative substituent are also included in the Gp useful in the invention.

Generally, each $R^1$ and $R^2$ is independently selected from the group consisting of carbalkoxy (2–6C), alkyl (1–6C) sulfonyl, aryl (6–10C) sulfonyl, aryl (6–10C); cyano; and —$CONR^5CO$— wherein $R^5$ is aryl (6–10C) or alkyl (1–6C);

each $R^3$ is independently carboxyalkyl (2–6C) or a salt, amide, ester or acylhydrazone thereof, or is alkyl (1–6C); and $R^4$ is $CHCH_2$, $CHOR^{4'}$, —CHO, —$COOR^{4'}$, $CH(OR^{4'})CH_3$, $CH(OR^{4'})CH_2OR^{4'}$, —$CH(SR^{4'})CH_3$, —$CH(NR^{4'}_2)CH_3$, —$CH(CN)CH_3$, —$CH(COOR^{4'})CH_3$, —$CH(OOCR^{4'})CH_3$, —$CH(halo)CH_3$, or —$CH(halo)CH_2$ (halo), wherein $R^{4'}$ is H, alkyl (1–6C) optionally substituted with a hydrophilic substituent, or wherein $R^4$ is an organic group of <12C resulting from direct or indirect derivatization of vinyl, or wherein $R^4$ is a group containing 1–3 tetrapyrrole-type nuclei of the formula —L—P as herein defined.

Figure 6A:
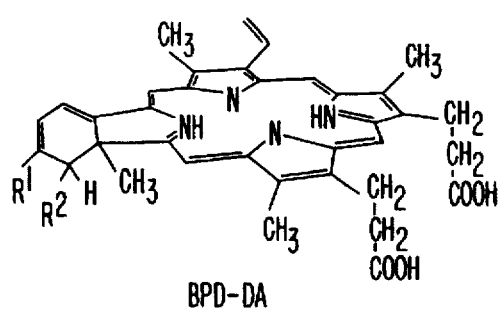
FIGS. 6A–6D show the structures of preferred green porphyrins—specifically BPD-MA, MPD-MD, BPD-DA and BPD-DB.
Figure 6B:
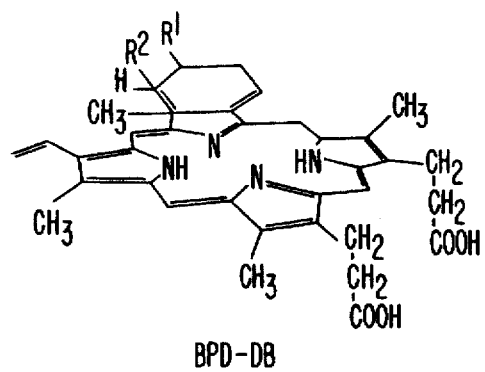
Figure 6C:
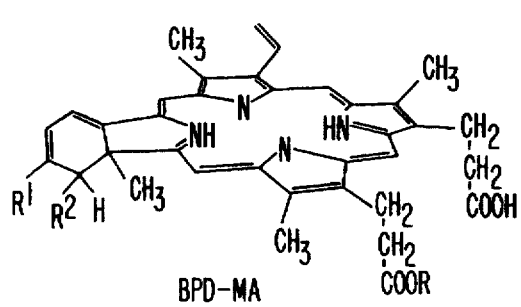
Figure 6D:
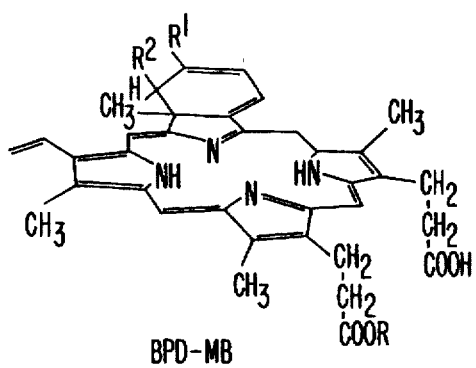

Compounds of the FIGS. 6C and 6D and mixtures thereof are particularly preferred. Also preferred are those wherein $R^1$ and $R^2$ are the same and are carbalkoxy, especially carboethoxy; also preferred are those wherein $R^4$ is —$CHCH_2$, $CH(OH)CH_3$ or —CH(halo) $CH_3$, or is a group containing 1–3 tetrapyrrole-type nuclei of the formula —L—P (defined below).

As used herein, "tetrapyrrole-type nucleus" represents a four-ring system of the skeleton:

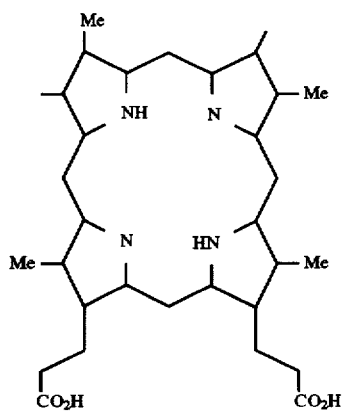

which is abbreviated

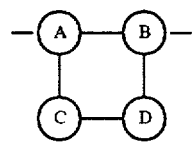

and a salt, ester, amide or acylhydrazone thereof, which is highly conjugated. It includes the porphyrin system, which is, in effect, a completely conjugated system, the chlorin system, which is, in effect, a dihydro form of the porphyrin, and the reduced chlorin system, which is a tetrahydro form of the completely conjugated system. When "porphyrin" is specified, the completely conjugated system is indicated; Gp is effectively a dihydro form of the porphyrin system.

One group of compounds is that wherein the substituent $R^4$ includes at least one additional tetrapyrrole-type nucleus. The resulting compounds of the invention are dimers or oligomers in which at least one of the tetrapyrrole-type ring systems is Gp. Linkage between the Gp moiety through the position of $R^4$ to an additional tetrapyrrole-type ring system may be through an ether, amine or vinyl linkage. Additional derivatization in the case of porphyrin ring systems which have two available substituent positions (in both A and B rings) corresponding to $R^4$ can also be formed, as further described below.

As stated above, the compounds of formulas shown in FIGS. 5A–5F include those wherein the embodiment of $R^4$ is formed by addition to the vinyl groups of initial Gp products. Thus, $R^4$ can be any substituent consistent with that formed by a facile addition reaction. Thus, both added substituents can be, for example, OH or halo, and these substituents can be further substituted, or the addition reagent may be of the form HX wherein H is added to the ring-adjacent carbon to provide $R^4$ of the form

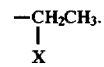

The vinyl group can also be oxidized to obtain $R^4$ as $CH_2OH$, —CHO, or COOH and its salts and esters.

Thus, in general $R^4$ represents any substituents to which the vinyl group —$CH=CH_2$ is readily converted by cleavage or addition, and further resultants of reaction of leaving groups with additional moieties. Typical $R^4$ substituents include:

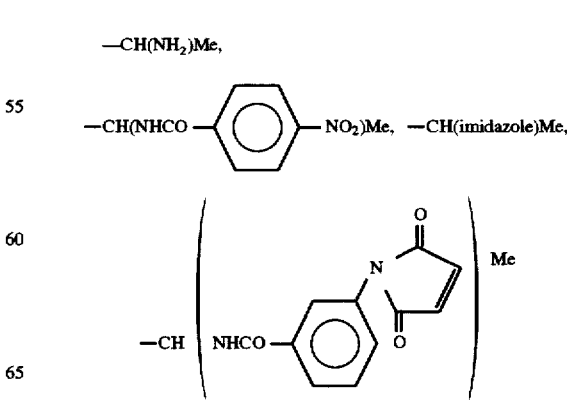

-continued

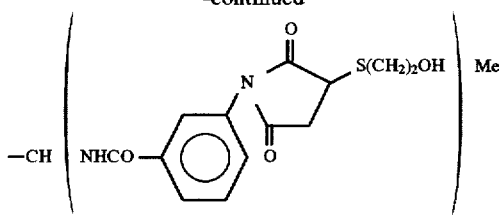

CH(OH)Me, —CHBrMe, —CH(OMe)Me, —CH (pyridinum bromide)Me, —CH(SH)Me and the disulfide thereof, —CHOHCH$_2$OH, —CHO, and —COOH or —COOMe.

When R$^4$ is —L—P, the substituent formula "—L—P" represents a substituent wherein —L— is selected the group consisting of

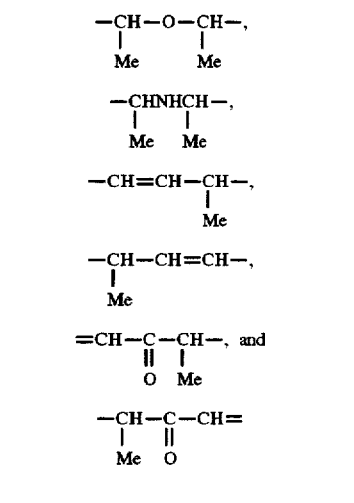

and P is selected from the group consisting of Gp wherein Gp is of the formulas shown in FIGS. 5A–5F, but lacking R$^4$ and conjugated through the position shown in FIGS. 5A–5F as occupied by R$^4$ to L, and a porphyrin of the formula

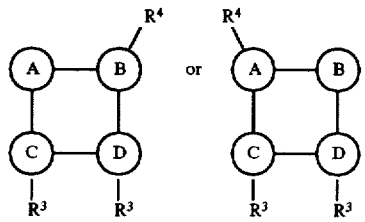

wherein R$^3$ and R$^4$ are as above-defined, and the unoccupied bond is then conjugated to L. It is understood that the abbreviation

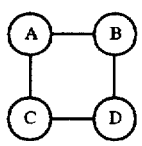

represents a porphyrin of the formula:

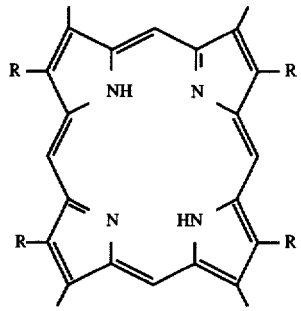

wherein each R is independently H or lower alkyl (1–4C).

(It is also understood that when —L— is of the formula (e) or (f), the ring system to which the double bond is attached will have a resonance system corresponding to

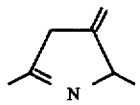

in the ring to which the double bond is attached, as shown.)

Preparation of the Dimers and Oligomers

The dimers and oligomeric compounds of the invention can be prepared using reactions analogous to those for dimerization and oligomerization of porphyrins per se. The green porphyrins or green porphyrin/porphyrin linkages can be made directly, or porphyrins may be conjugated, flowed by a Diels-Alder reaction of either or both terminal porphyrins to convert to the corresponding green porphyrin.

The following examples are intended to illustrate but not to limit the invention.

EXAMPLE 1

Response of Various Leukocytes to BPD and Irradiation

Blood was withdrawn from two patients who were shown to be infected with HIV. Whole blood from each patient was brought to varying concentrations with BPD-MA and then irradiated with light at 10.8 J/cm$^2$ using 690 nanometers light emitted from LEDs over 4 minutes. The populations of various subsets of T-cells were evaluated by flow cytometry in comparison to untreated controls and the percentage of cells present as a percent of control plotted as a function of BPD-MA concentration.

The results are shown in FIGS. 1A and 1B. As indicated, most cell populations remained relatively constant, including B-cells and CD4$^+$ cells. Slight decreases were shown in CD8$^+$ cells and DR$^+$ cells. IL-2R$^+$ cells show a dramatic decrease in the patient results shown in FIG. 1A which is dose-dependent on BPD-MA.

As shown in FIG. 1A, although IL-2R$^+$ cells are dramatically decreased, significant decreases for DR$^+$ and CD8$^+$ cells are also shown. The effect on DR$^+$ cells is more dramatically shown for the second patient in FIG. 1B.

Similar studies were conducted with a constant concentration of BPD-MA (0.5 µg/ml) using as subjects a normal subject and two HIV patients. FIG. 2 shows the subpopulations of leukocytes in untreated blood from these three donors. As shown in FIG. 2, B-cells and natural killer cells occur at roughly the same levels in normal and HIV patients; however, ARC patients consistently show diminished levels of $CD4^+$ and elevated levels of $CD8^+$, $DR^+$ and $IL-2R^+$.

Figure 3A:
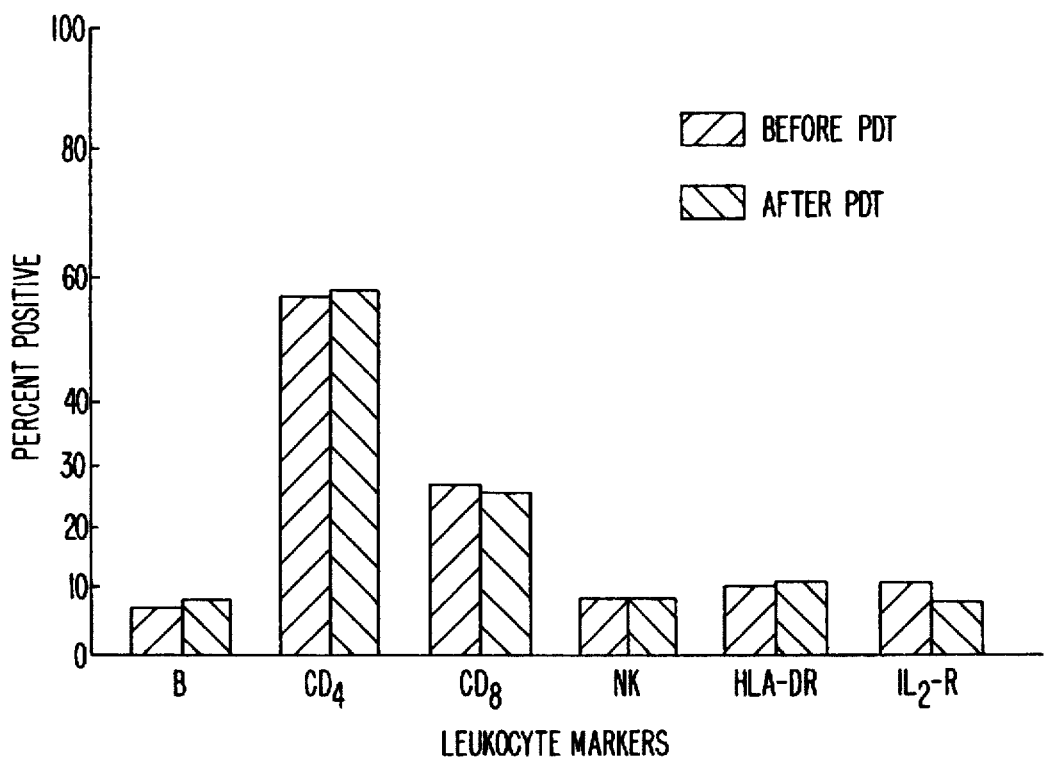
FIGS. 3A and 3B show the relative concentrations of subsets of leukocytes in blood from a normal donor and an HIV donor, respectively, before and after treatment with BPD and irradiation.
Figure 3B:
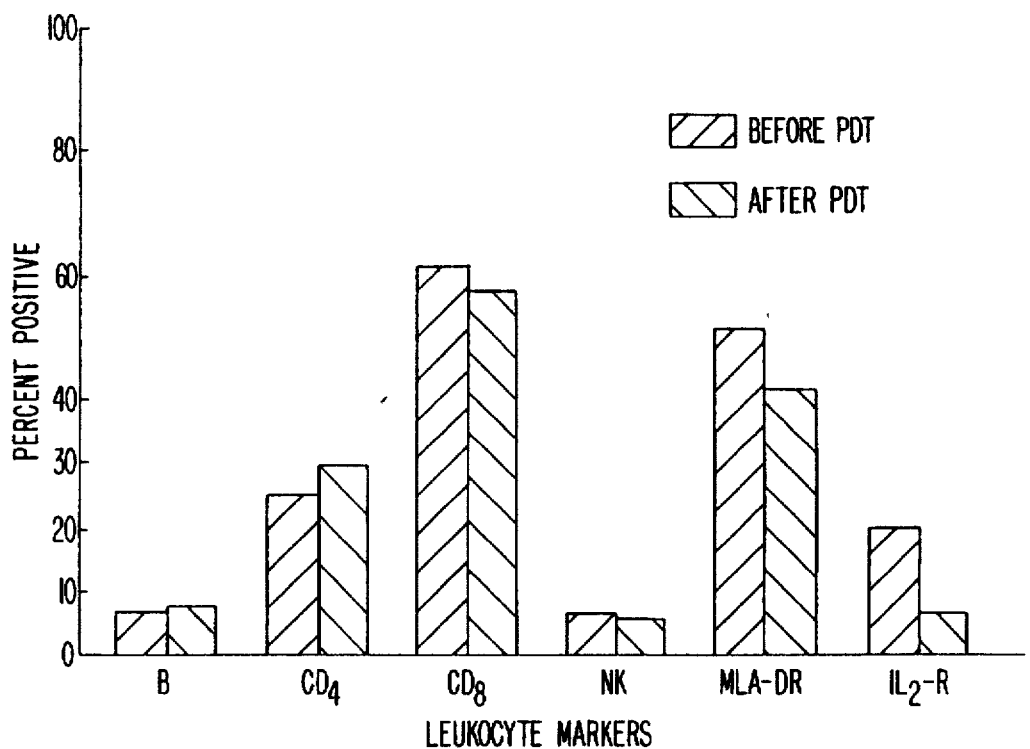
Figure 3C:
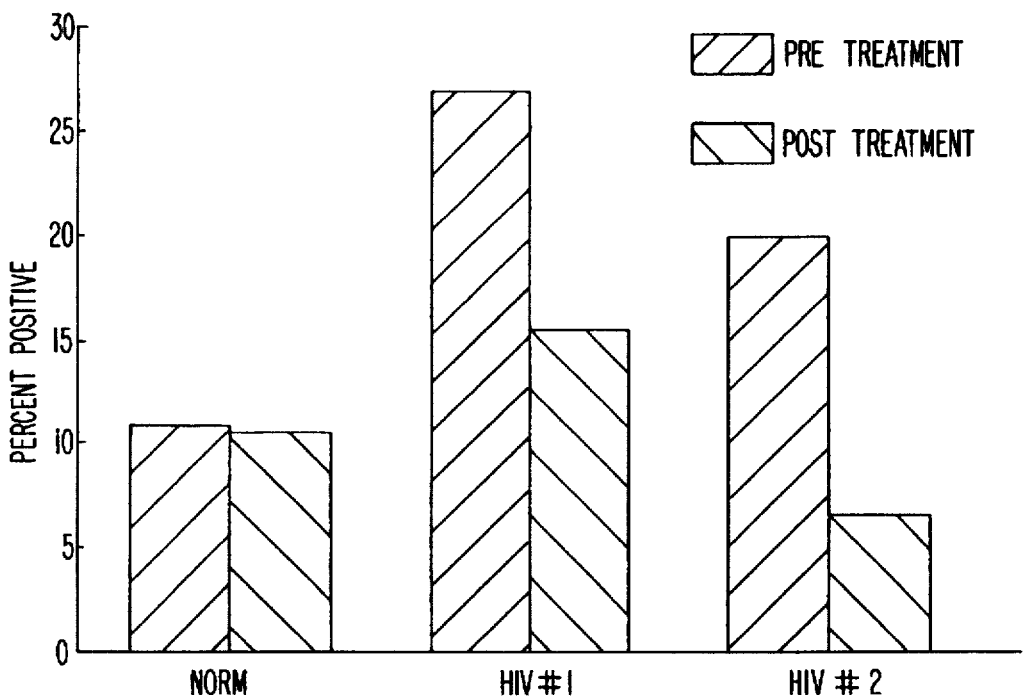
FIG. 3C shows the levels of $IL-2R^+$ cells specifically before and after treatment with BPD and irradiation in normal and HIV-infected subjects.

FIGS. 3A, 3B, and 3C show the effects of the treatment of the invention. As shown in FIG. 3A, treatment of leukocyte subpopulations in normal blood has little effect on any of the populations shown. FIG. 3B shows that when HIV-infected blood is subjected to this treatment, there is a slight diminution in $CD8^+$, a slight diminution in $DR^+$, and a significant decrease in $IL-2R^+$ cells. FIG. 3C shows these results specifically for $IL-2R^+$ cells both for normals and for two HIV-infected patients. Again, the dramatic decrease is shown.

Thus, after treatment with 0.5 µg/ml BPD for 4 minutes in the presence of 10.8 $J/cm^2$ of light centered at 690 nanometer, the cell populations of all of the cell types in the normal subject, and all cell types except for $IL-2R^+$ in the HIV patients remains relatively constant. $DR^+$ and $CD8^+$ cells are slightly decreased. The BPD/light treatment seems to have little or no effect on most subclasses of leukocytes; however, the elevated levels of $IL-2R^+$ cells are restored to normal.

EXAMPLE 2

Figure 4:
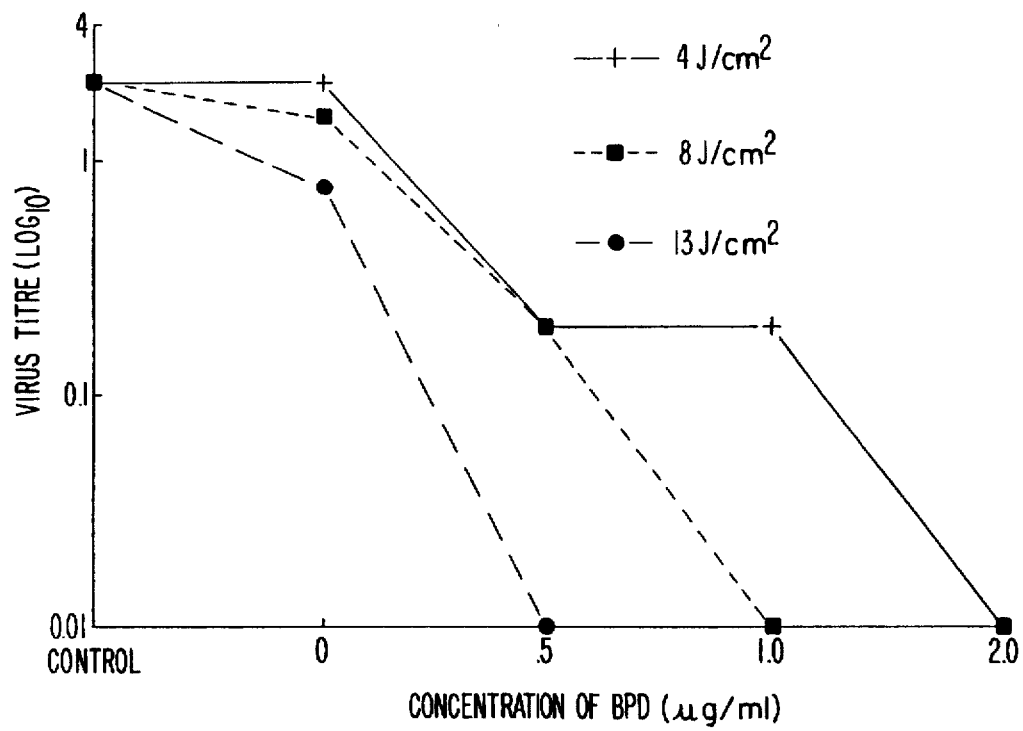
FIG. 4 shows inactivation of cell-associated HIV in naturally infected human blood by treatment with BPD and irradiation.

Whole human blood from an HIV patient was also subjected to the treatment using various concentrations of BPD and various light intensities in a protocol similar to that set forth in Example 1 and the effect on inactivation of cell-associated HIV was tested. The results are shown in FIG. 4. As shown, intensities of 13 $J/cm^2$ gave dramatic inactivation of the virus at concentrations of BPD at about 0.5 µg/ml or less. Lower intensities of radiation required higher concentrations of BPD completely to inactivate the virus.

EXAMPLE 3

Inactivation of free HIV (LAV-1 strain) in tissue culture of CEM cells was also tested. In the assay, LAV-1 stock was diluted into the tissue culture medium and BPD was added at either 0.25 µg/ml or 0.5 µg/ml. The media were incubated for 1 hour and exposed to 3 minutes of irradiation centered at 690 nm at an intensity of 10.8 $J/cm^2$. The media were then added to CEM cells and the cells were assayed after 6 days of culture using a standard p24 assay. The results are read in terms of pg/ml.

The results are shown in Table 1. As shown, at dilutions of LAV that provided high levels of p24, treatment with BPD at either 0.25 µg/ml or 0.5 µg/ml was able substantially to lower the level of p24 determined.

TABLE 1

| LAV-1 DILUTION | TREATMENT No Drug no light | x̄ pg/ml (p24) TREATMENT .25 µg BPD 3 min | TREATMENT .5 µg BPD 3 min |
|---|---|---|---|
| $10^{-2}$ | >616 | 23.2 | 14.2 |
| $3 \times 10^{-2}$ | >616 | 18.2 | 14.5 |
| $5 \times 10^{-2}$ | >616 | 15.1 | 11.4 |
| $7 \times 10^{-2}$ | >616 | 8.9 | 7.6 |
| $9 \times 10^{-2}$ | >616 | 7.6 | 5.4 |
| $10^{-3}$ | >616 | 4.5 | 7.0 |
| $3 \times 10^{-3}$ | >616 | 5.1 | 3.2 |
| $5 \times 10^{-3}$ | >616 | 4.5 | 3.9 |
| $7 \times 10^{-3}$ | >616 | 3.9 | 2.0 |
| $9 \times 10^{-3}$ | >616 | 5.4 | 2.3 |
| $10^{-4}$ | >616 | 2.0 | 4.2 |
| $3 \times 10^{-4}$ | >616 | 3.6 | 2.0 |

TABLE 1-continued

| LAV-1 DILUTION | TREATMENT No Drug no light | x̄ pg/ml (p24) TREATMENT .25 µg BPD 3 min | TREATMENT .5 µg BPD 3 min |
|---|---|---|---|
| $5 \times 10^{-4}$ | >616 | 2.9 | 2.3 |
| $7 \times 10^{-4}$ | >616 | 3.2 | — |
| $9 \times 10^{-4}$ | 2.6 | 2.6 | — |

I claim:

1. A method for selectively reducing the activated leukocyte cell population in the leukocyte-containing fluid of a subject in need of such reduction, which method comprises:

treating said fluid or an activated leukocyte-containing fraction thereof with an effective amount of a green porphyrin (Gp) compound, and irradiating said treated fluid or fraction with light comprising at least one wavelength absorbed by said Gp compound.

2. The method of claim 1 wherein said treating is effected with a Gp concentration of about 0.05–5 µg/ml.

3. The method of claim 2 wherein said treating is effected with a Gp concentration of about 0.1–1 µg/ml.

4. The method of claim 3 wherein said treating is effected with a Gp concentration of about 0.5 µg/ml.

5. The method of claim 1 wherein said Gp has a formula selected from the group consisting of

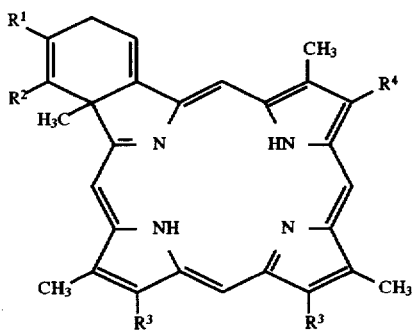

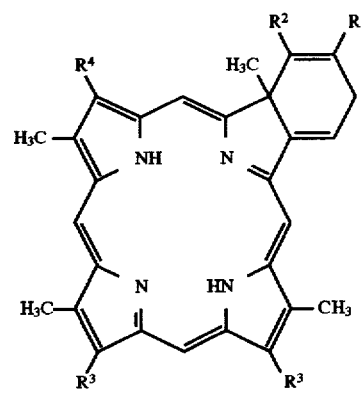

-continued

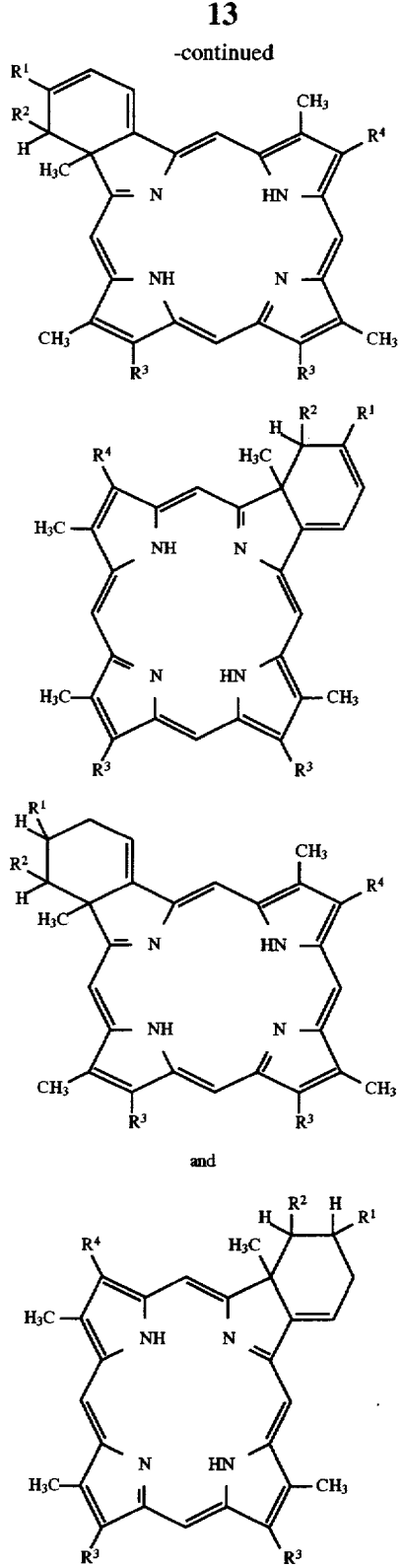

and

6. The method of claim 5 wherein $R^1$ and $R^2$ are carbomethoxy or carboethoxy.

7. The method of claim 6 wherein each $R^3$ is —$CH_2CH_2COOH$— or a salt, amide, ester or acyl hydrazone thereof.

8. The method of claim 5 wherein said Gp is of formula 3 or 4.

9. The method of claim 8 wherein said Gp has a formula selected from the group consisting of

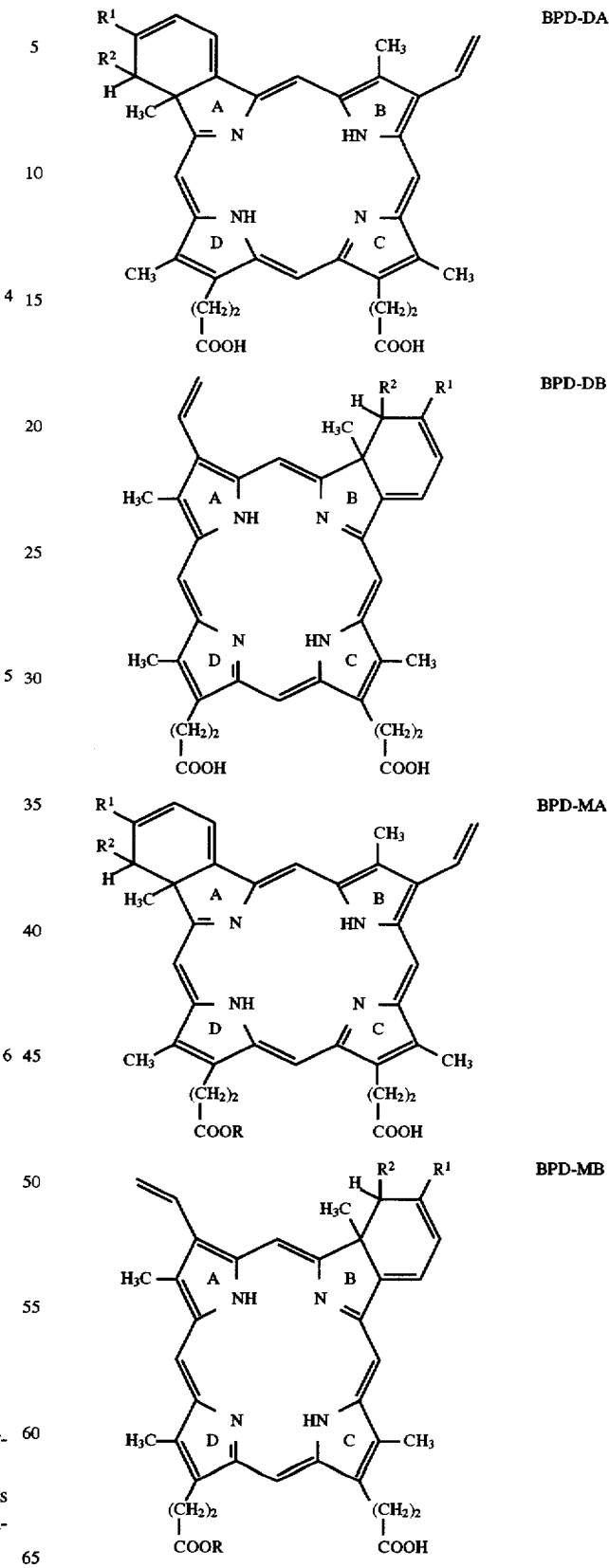

wherein each of $R^1$ and $R^2$ is independently selected from carbomethoxy and carboethoxy, and R is methyl or ethyl.

10. Body fluid or a fraction thereof which has been depleted of activated leukocytes by the method of claim 1.

11. The body fluid or fraction thereof of claim 10 wherein the body fluid is blood or a fraction thereof which contains elevated levels of $CD8^+$ cells and of $DR^+$ cells, but normal levels of $IL-2R^+$ cells.

12. A method to treat a patient with autoimmune disease which method comprises treating at least a portion of said patient's leukocyte-containing body fluid or a fraction thereof containing activated leukocytes with an effective amount of a green porphyrin (Gp) compound, and irradiating said treated fluid with light comprising at least one wavelength absorbed by said Gp compound.

* * * * *

UNITED STATES PATENT AND TRADEMARK OFFICE
CERTIFICATE OF CORRECTION

PATENT NO. : 5,776,966
DATED : 07 July 1998
INVENTOR(S) : NORTH et al.

It is certified that error appears in the above-identified patent and that said Letters Patent is hereby corrected as shown below:

- on the Title Page, line 2: "North" should read --North et al.--;

- on the Title Page, after [75] Inventors: "Janice North, Vancouver; Canada" should read --Janice North, Vancouver; Julia G. Levy, Vancouver--.

Signed and Sealed this

Twentieth Day of July, 1999

Attest:

Q. TODD DICKINSON

Attesting Officer

Acting Commissioner of Patents and Trademarks